(12) United States Patent
Woodside et al.

(10) Patent No.: US 9,701,935 B2
(45) Date of Patent: Jul. 11, 2017

(54) MAGNETIC PARTICLES

(75) Inventors: Steven M. Woodside, Calgary (CA); Graeme Milton, North Vancouver (CA); Jason Dowd, Brampton (CA)

(73) Assignee: StemCell Technologies Inc., Vancouver, British Columbia (CA)

( * ) Notice: Subject to any disclaimer, the term of this patent is extended or adjusted under 35 U.S.C. 154(b) by 1790 days.

(21) Appl. No.: 12/937,553

(22) PCT Filed: Apr. 16, 2009

(86) PCT No.: PCT/CA2009/000468
§ 371 (c)(1),
(2), (4) Date: Dec. 21, 2010

(87) PCT Pub. No.: WO2009/127045
PCT Pub. Date: Oct. 22, 2009

(65) Prior Publication Data
US 2011/0111982 A1    May 12, 2011

Related U.S. Application Data

(60) Provisional application No. 61/045,343, filed on Apr. 16, 2008.

(51) Int. Cl.
*C12N 1/02* (2006.01)
*C40B 30/10* (2006.01)
(Continued)

(52) U.S. Cl.
CPC .............. *C12N 1/02* (2013.01); *A61K 9/5042* (2013.01); *A61K 9/5094* (2013.01); *B03C 1/01* (2013.01);
(Continued)

(58) Field of Classification Search
CPC ......... B03C 1/01; B03C 2201/26; B82Y 5/00; B82Y 25/00; C12N 1/02; C12N 11/10;
(Continued)

(56) References Cited

U.S. PATENT DOCUMENTS 4,452,773 A * 6/1984 Molday ........................ 424/1.37
4,868,109 A 9/1989 Lansdorp
(Continued)

FOREIGN PATENT DOCUMENTS

| CN | 11029138 | 5/2007 |
|----|----------|--------|
| WO | WO8301738 | 5/1983 |

(Continued)

OTHER PUBLICATIONS

Article—Safarik et al "Use of magnetic techniques for the isolation of cells", Journal of Chromatography B, vol. 722, No. 1-2, Feb. 5, 1999, pp. 33-53, XP004156204.

*Primary Examiner* — Mark Shibuya
*Assistant Examiner* — Nam Nguyen
(74) *Attorney, Agent, or Firm* — Bereskin & Parr LLP/S.E.N.C.R.L., s.r.l.; Micheline Gravelle

(57) ABSTRACT

A magnetic particle comprises a polysaccharide matrix and a plurality of magnetic crystals dispersed in the matrix. A method for making magnetic particles comprises combining a basic solution with a metal ion solution and allowing the metal ions to oxidize to form magnetic crystals, and combining the magnetic crystals with a polysaccharide solution to form the magnetic particles.

12 Claims, 3 Drawing Sheets

(51) Int. Cl.
*H01F 1/11* (2006.01)
*B82Y 5/00* (2011.01)
*B82Y 25/00* (2011.01)
*C12N 11/10* (2006.01)
*G01N 33/543* (2006.01)
*C08L 1/00* (2006.01)
*C08L 3/00* (2006.01)
*C08L 5/00* (2006.01)
*C08L 5/02* (2006.01)
*A61K 9/50* (2006.01)
*B03C 1/01* (2006.01)
*H01F 1/00* (2006.01)

(52) U.S. Cl.
CPC ............. *B82Y 5/00* (2013.01); *B82Y 25/00* (2013.01); *C08L 1/00* (2013.01); *C08L 3/00* (2013.01); *C08L 5/00* (2013.01); *C08L 5/02* (2013.01); *C12N 11/10* (2013.01); *G01N 33/5434* (2013.01); *H01F 1/0063* (2013.01); *B03C 2201/26* (2013.01); *C08K 2201/01* (2013.01)

(58) Field of Classification Search
CPC ...... C08L 1/00; C08L 3/00; C08L 5/00; C08L 5/02; G01N 33/5434; H01F 1/0063; H01F 1/11; C08K 2201/01; A61K 9/5031; A61K 9/5094; C40B 30/10
USPC ................................................. 436/518, 526
See application file for complete search history.

(56) References Cited

U.S. PATENT DOCUMENTS

| | | | | |
|---|---|---|---|---|
| 5,190,635 | A | * | 3/1993 | Hettinger ............ C10G 11/182 208/113 |
| 5,720,939 | A | | 2/1998 | Schroder |
| 6,123,920 | A | * | 9/2000 | Gunther ............... A61K 49/049 424/9.322 |
| 6,321,105 | B1 | * | 11/2001 | Jenkins ................. G01R 33/50 324/307 |
| 6,423,296 | B1 | | 7/2002 | Gunther et al. |
| 2003/0007942 | A1 | * | 1/2003 | Koenig .................... A61K 8/19 424/70.1 |
| 2003/0225033 | A1 | | 12/2003 | Groman et al. |
| 2006/0025713 | A1 | * | 2/2006 | Rosengart et al. .......... 604/5.02 |
| 2007/0225488 | A1 | | 9/2007 | Skold |

FOREIGN PATENT DOCUMENTS

| WO | WO8504330 | 10/1985 |
|---|---|---|
| WO | WO8903675 A1 | 5/1989 |
| WO | WO03005029 | 1/2003 |
| WO | WO2007079276 | 7/2007 |

\* cited by examiner

MAGNETIC PARTICLES

FIELD

The disclosure relates to magnetic particles usable for cell separation. More specifically, the disclosure relates to magnetic particles with low light scatter properties.

BACKGROUND

In many applications it is desirable to enrich, or alternatively deplete, certain cell populations in a biological sample. For example, the separation of specific cell types from peripheral blood, bone marrow, spleen, thymus and fetal liver is key to research in the fields of hematology, immunology and oncology, as well as diagnostics and therapy for certain malignancies and immune disorders.

Investigation of cellular, molecular and biochemical processes requires analysis of certain cell types in isolation. For example purified populations of immune cells such as T cells and antigen presenting cells are necessary for the study of immune function and are used in immunotherapy. Most cell separation techniques require that the input sample be a single cell suspension. For this reason, blood has historically been the most common tissue used for cell separations. Numerous techniques have been used to isolate T cell subsets, B cells, basophils, NK cells and dendritic cells from blood for these investigations.

More recently, enzymatic digestion methods have been developed to dissociate tissues from solid organs into single cell suspensions, permitting distinct cell types to be isolated. This is of particular benefit to the study of pluripotent stem cells and tissue-specific stem cells from adults. The rapidly growing field of stem cell research is spurred by the potential of these cells to repair diseased or damaged tissues. Bone marrow (hematopoietic) stem cells were the first adult stem cells to be purified and used clinically and the therapeutic potential of hematopoietic stem cells is now well documented. Transplantation of hematopoietic cells from peripheral blood and/or bone marrow is increasingly used in combination with high-dose chemo- and/or radiotherapy for the treatment of a variety of disorders including malignant, non-malignant and genetic disorders. Very few cells in such transplants are capable of long-term hematopoietic reconstitution, and thus there is a strong stimulus to develop techniques for purification of hematopoietic stem cells. Furthermore, serious complications and indeed the success of a transplant procedure is to a large degree dependent on the effectiveness of the procedures that are used for the removal of cells in the transplant that pose a risk to the transplant recipient. Such cells include T lymphocytes that are responsible for graft versus host disease (GVHD) in allogeneic grafts, and tumor cells in autologous transplants that may cause recurrence of the malignant growth. It is also important to debulk the graft by removing unnecessary cells and thus reducing the volume of cyropreservant to be infused.

In certain instances it is desirable to remove or deplete tumor cells from a biological sample, for example in bone marrow transplants. Epithelial cancers of the bronchi, mammary ducts and the gastrointestinal and urogenital tracts represent a major group of solid tumors seen today. Micrometastatic tumor cell migration is thought to be an important prognostic factor for patients with epithelial cancer (Braun et al., 2000; Vaughan et al., 1990). The ability to detect such metastatic cells is limited by the effectiveness of tissue or fluid sampling and the sensitivity of tumor detection methods. A technique to enrich circulating epithelial tumor cells in blood samples would increase the ability to detect metastatic disease and facilitate the study of such rare cells to determine the biological changes which enable spread of the disease.

Hematopoietic cells and immune cells have been separated on the basis of physical characteristics such as density and on the basis of susceptibility to certain pharmacological agents which kill cycling cells. The advent of monoclonal antibodies against cell surface antigens has greatly expanded the potential to distinguish and separate distinct cell types. There are two basic conceptual approaches to separating cell populations from blood and related cell suspensions using monoclonal antibodies. They differ in whether it is the desired or undesired cells which are distinguished/labeled with the antibody(s).

In positive selection techniques the desired cells are labeled with antibodies and removed from the remaining unlabeled/unwanted cells. In negative selection, the unwanted cells are labeled and removed. Antibody/complement treatment and the use of immunotoxins are negative selection techniques, but Fluorescence Activated Cell Sorting (FACS) and most batch-wise immunoadsorption techniques can be adapted to both positive and negative selection. In immunoadsorption techniques, cells are selected with monoclonal antibodies and preferentially bound to a surface which can be removed from the remainder of the cells e.g. column of beads, flask, magnetic particles. Immunoadsorption techniques have won favor clinically and in research because they maintain the high specificity of cell targeting with monoclonal antibodies, but unlike FACS, they can be scaled up to directly process the large numbers of cells in a clinical harvest and they avoid the dangers of using cytotoxic reagents such as immunotoxins and complement.

Magnetic separation is a process used to selectively retain magnetic materials within a vessel, such as a centrifuge tube or column, in a magnetic field gradient. Targets of interest, such as specific biological cells, can be magnetically labelled by binding of magnetic particles to the surface of the targets through specific interactions including immuno-affinity interactions. Other useful interactions include drug-drug receptor, antibody-antigen, hormone-hormone receptor, growth factor-growth factor receptor, carbohydrate-lectin, nucleic acid sequence-complementary nucleic acid sequence, enzyme-cofactor or enzyme-inhibitor binding. The suspension, containing the targets of interest within a suitable vessel, is then exposed to magnetic field gradients of sufficient strength to separate the targets from other entities in the suspension. The vessel can then be washed with a suitable fluid to remove the unlabeled entities, resulting in a purified suspension of the targets of interest.

The majority of magnetic labeling systems use superparamagnetic particles with antibodies or streptavidin covalently bound to their surface. In cell separation applications these particles can be used for either positive selection, where the cells of interest are magnetically labelled, or negative selection where the majority of undesired cells are magnetically labelled. Magnetic separation applications where the targets of interest are proteins or nucleic acids would be considered positive selection approaches since the entity of interest is typically captured on the magnetic particle. The diameter of the particle used varies widely from about 50-100 nm for MACS particles (Miltenyi Biotec) and StemSep™ colloid (StemCell Technologies), through 150 nm-1.5 µm for Easy-Sep™ (StemCell Technologies) and Imag (BD Biosciences) particles and 1 to 4.2 µm for Dynabeads (Invitrogen). The type of particle used is influenced by the magnet technology employed to separate the labelled entities.

There are two important classes of magnetic separation technologies, both of which, for convenience and practical reasons use permanent magnets as opposed to electromagnets. The first class is column-based high-gradient-magnetic-field separation technology that uses small, weakly magnetic particles to label the targets of interest, and separates these targets in a column filled with a magnetizable matrix. Very high gradients are generated close to the surface of the matrix elements when a magnetic field is applied to the column. The high gradients are necessary to separate targets labelled with these relatively weakly magnetic particles. The second class is tube-based technology that uses more strongly magnetic particles to label the targets of interest. These targets of interest are then separated within a centrifuge-type tube by magnetic field gradients generated by a magnet outside the tube. This method has the advantage that it does not rely on a magnetizable matrix to generate the gradients and therefore does not required an expensive disposable column or a reusable column with an inconvenient cleaning and decontamination procedure.

Once placed within the magnet, targeted cells migrate toward the region or regions of highest magnetic field strength and are retained within the magnetic field while the unlabeled cells are drawn off. The targeted cells can then be collected and used in the desired application after removal from the magnetic field. In the event that negative selection is required, the unlabeled cells are drawn off and can be utilized for a variety of applications such as cell sorting.

The EasySep labeling method uses a tetrameric antibody complex (TAC) (U.S. Pat. No. 4,868,109). TACs are comprised of two mouse IgG1 monoclonal antibodies held in tetrameric array by two rat anti-mouse IgG1 antibody molecules. EasySep™ reagents cross-link magnetizable particles to cells of interest using TAC where one mouse antibody targets the particles and the other targets surface markers on the cells of interest. The EasySep™ magnet then separates the magnetically labeled cells from non-labeled cells within a standard centrifuge tube.

After magnetic labeling and initial magnetic separation, it is necessary to wash away non-specifically separated cells to attain the desirable level of fractionation of the sample into labeled and unlabeled cells. In tube-based systems such as Dynal® and EasySep®, the separation vessel is typically a standard centrifuge tube held in a magnetic field. To obtain high purity of the target cells in positive selection applications, a sequence of batch wash steps is used to remove unlabelled cells from the separation tube, where the supernatant containing the majority of unlabeled cells is removed from the separation vessel and then the retained cells are resuspended and re-separated a number of times as required.

Larger magnetic particles (>0.5 µm) have the advantage that separation times can be lower, and weaker magnetic fields can be used. For example, Dynal particles of 1.0, 2.5 and 4.2 µm diameter are separated by a simple side-pull magnet with a peak magnetic field strength of about 0.3 T. Polysciences BioMag Plus particles of 1.0 µm diameter may be separated in 96-well plates using a pull-down plate magnet such as Dexter Magnetics LifeSep 96F. However, it is well known that larger magnetic particles also strongly affect the light scatter signature of the cells to which they are bound when analyzed by FACS. Larger particles bound to cells affect both the forward scatter and side scatter signal, with the side scatter signal being more severely affected. The forward scatter signal correlates to cell size, while the side scatter signal correlates to granularity. Forward and side scatter signals are important component of FACS analysis and distortion of these signals can significantly impair the interpretation of the results. A large magnetic particle that, when bound to cells, does not exhibit this effect on the light scattering property of the cells would be of high utility for magnetic cell separation protocols. Larger particles also interfere with visible light microscopy of the cells by changing the apparent cell morphology. A large particle that, when bound to cells, does not appreciably change the apparent morphology of the cells when viewed by visible light microscopy would also be of high utility for magnetic cell separation protocols.

SUMMARY

The present application relates to magnetic particles, methods of making magnetic particles and use of magnetic particles with low light scatter properties.

According to one broad aspect, a magnetic particle is provided which comprises a matrix of polysaccharide, and a plurality of magnetic crystals dispersed in the matrix. It has been determined that a magnetic particle in accordance with this broad aspect may exhibit low light scattering properties, even at diameters larger than 0.5 microns. More particularly, the magnetic particles may have a diameter greater than about 0.5 micron, may respond to a weak magnetic field, and may, when linked to a plurality of cells, cause a shift in the side scatter signal of the cells of less than 100% as detected by flow cytometry In some embodiments, the diameter of the magnetic particle is between 0.5 and 10 microns. More particularly, the diameter may be between 0.9 and 2.5 microns.

In some embodiments, the magnetic crystals comprise 60 to 85 wt % of the particle. More particularly, the magnetic crystals may comprise 75 to 83 wt % of the particle.

In some embodiments, the magnetic crystals comprise a transition metal oxide, such as an iron oxide. For example, the transition metal oxide may comprise at least one of $Fe_2O_3$ and $Fe_3O_4$.

In some embodiments, the magnetic crystals may have a crystal diameter of between 5 nm and 50 nm.

In some embodiments, the polysaccharide is dextran.

In some embodiments, the magnetic crystals are uniformly dispersed in the matrix.

According to another broad aspect, a method is provided for making magnetic particles. The method comprises combining a basic solution with a metal ion solution and allowing the metal ions to oxidize to form magnetic crystals; and combining the magnetic crystals with a polysaccharide solution and allowing the magnetic particles to form.

Preferably, the magnetic particles formed by this method comprise a matrix of polysaccharide and a plurality of magnetic crystals dispersed in the matrix.

In some embodiments, the basic solution has a pH of at least 9.5.

In some embodiments, the basic solution and the metal ion solution are combined at a volumetric ratio of between 1:1 and 5:1.

In some embodiments, the basic solution and the metal ion solution are combined to form a mixture having a pH of about 10.5.

In some embodiments, the basic solution and the metal ion solution are combined by flow-mixing.

In some embodiments, the method further comprises reducing an average diameter of the magnetic particles by disaggregation to between 0.5 and 10 microns, and more particularly, to between 0.9 and 2.5 microns. In some further embodiments, the diameter is reduced by one of membrane extrusion and homogenization.

In some embodiments, the basic solution is ammonium hydroxide. In some embodiments, metal ion solution comprises at least one of cobalt, manganese, nickel, iron, and alloys thereof. In some embodiments, the metal solution is an iron solution. In further embodiments, the iron solution comprises 1 part $Fe^{2+}$ to 2 parts $Fe^{3+}$.

In some embodiments, the basic solution and the iron solution are allowed to flow together for a period time. In some embodiments, the period of time is more than about 0.1 seconds and less than about 180 seconds, and more particularly, more than about 0.1 seconds and less than about 0.5 seconds.

In some embodiments, the polysaccharide solution comprises at least one of starch, dextran, hetastarch, cellulose and partially or fully substituted amino-dextran. In the preferred embodiment, the polysaccharide solution comprises dextran.

In another broad aspect, a method is provided for magnetic particles for separating a first population of cells from a second population of cells suspended in fluid. The method comprises linking the magnetic particles to the first population of cells; placing the first and second populations of cells in a magnetic field and; recovering one of the first or second populations of cells.

In some embodiments, the magnetic particles are linked to the first population of cells using tetrameric antibody complexes.

In some embodiments, the method further comprises analyzing said first population of cells by FACs, wherein a shift in a side scatter signal of the first population of cells when bound to the magnetic particles is less than 100%.

BRIEF DESCRIPTION OF THE DRAWINGS

These and other advantages will be more fully and particularly understood in connection with the following description in which.

DETAILED DESCRIPTION

Figure 1:
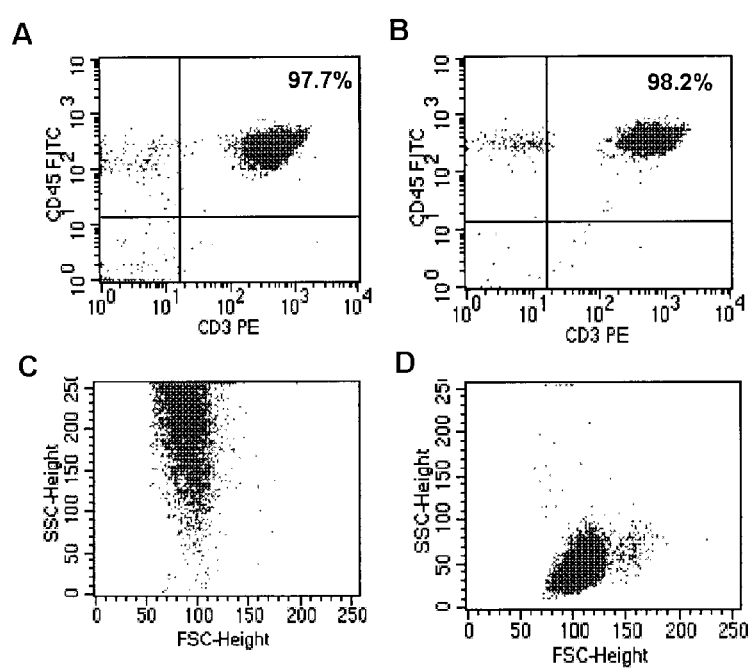
FIG. 1 is a graph showing side scatter effect on cells purified by CD3 positive selection using exemplary particles described herein compared to EasySep® Microparticles. Panels A, B are representative FACS plots of cells following CD3 positive selection analysed for expression of CD3 and CD45 antigens. Panels C, D are representative FACS plots of the forward vs. side scatter profile of CD3 selected cells. Panels A and C depict cells selected with EasySep® Microparticles. Panels B and D depict cells selected with Particles described herein.

The disclosure relates to magnetic particles, methods of making magnetic particles and use of magnetic particles. The particles may comprise a a matrix of polysaccharide and a plurality of magnetic crystals dispersed in the matrix. As used herein, the term 'magnetic particles' refers to particles that respond to a magnetic field. In some embodiments, magnetic particles may have a diameter of between 0.5 microns and 10 microns. More particularly, the magnetic particles may have a diameter of between 0.9 microns and 2.5 microns. In such embodiments, the particles may allow for relatively short cell separation times, and may allow for the use of relatively low magnetic fields (e.g. less than 20 T/m). Further, in such embodiments, magnetic particles may exhibit a relatively low effect on forward and side scatter when the cells bound thereto are analyzed by FACS.

According to one embodiment of the method, as a first step, magnetic crystals are formed by combining a metal ion solution and a basic solution and allowing the metal ions to oxidize.

The metal ion solution may comprise a transition metal, for example, one or more of iron, cobalt, manganese and nickel, and alloys thereof. Preferably, the metal ion solution is an iron salt solution. The iron salt solution may have, for example, a total iron concentration of between about 8 mM and about 231 mM.

The iron solution may comprise various iron compounds. Preferably, the iron solution comprises an iron oxide. More preferably, the iron solution comprises $Fe^{2+}$ and $Fe^{3+}$. For example, the iron solution may comprise iron (II) chloride tetrahydrate and iron (III) chloride hexahydrate in water at approximately a 1:2 $Fe^{2+}:Fe^{3+}$ molar ratio. In alternate embodiments, the iron solution may comprise iron (II) sulfate tetrahydrate, iron (II) acetate, iron (II) acetylacetonate, iron (II) bromide, iron (II) iodide, iron (III) iodide, iron (III) phosphate, iron (III) nitrate iron (III) bromide, iron (III) acetylacetonate, iron (III) sulfate pentahydrate or other solutions of iron containing compounds where the $Fe^{2+}:Fe^{3+}$ molar ratio is approximately 1:2.

In some embodiments, the basic solution has a pH of at least 9.5. In the preferred embodiment, the basic solution has a pH of 11 to 11.5. Preferably, the basic solution comprises aqueous ammonium hydroxide ($NH_4OH$). In alternate embodiments, the basic solution may comprise, for example, sodium hydroxide (NaOH), potassium hydroxide (KOH) or another Bronsted-Lowry base.

The metal ion solution and the basic solution may be combined in a variety of ways, and at a variety of volumetric ratios. For example, the metal ion solution and the basic solution may be combined at a volumetric ratio of between about 1:1 and about 5:1. The solutions are preferably combined such that the pH of the resulting mixture is at least about 9.5, more preferably between 9.5 and 13.5, and most preferably about 10.5.

Preferably, the metal ion solution and the basic solution are combined by flow-mixing, and are allowed to flow together for a period of time in order for the metal ions to oxidize and the magnetic crystals to form. For example, the metal ion solution and the basic solution may be pumped through respective first and second pieces of tubing to a junction, where they mix and flow into a third piece of tubing. As the solutions mix and pass through the third piece of tubing, the metal ions may oxidize in the presence of the base to form magnetic crystals. Preferably, the solutions are allowed to flow together for between about 0.1 seconds and about 180 seconds, and more particularly, between abut 0.1 seconds and about 5 seconds. For example, the third piece of tubing may be sized such that the transit time therethrough is about 0.1 seconds.

In some embodiments, in addition to or instead of being allowed to flow together after mixing, the mixture of the basic solution and the metal ion solution may be incubated in a vessel, either with or without further mixing or agitation.

In further alternate embodiments, rather than flow mixing, the metal ion solution and the basic solution may be combined in a batch process by addition to a vessel, followed by agitation.

The step of combining the metal ion solution and the basic solution may be carried out at a variety of temperatures. For example, the step of combining the metal ion solution and the basic solution may be carried out at temperatures between room temperature and 95° C. Preferably, the step of combining the metal ion solution and the basic solution is carried out at temperatures less than 50° C.

The magnetic crystals preferably have a diameter of between 5 nm and 50 nm.

When the magnetic crystals have formed, they are combined with a polysaccharide solution and the magnetic particles are allowed to form. The polysaccharide solution may be an aqueous solution of, for example, starch, dextran, hetastarch, cellulose, partially or fully substituted aminodextran, and combinations thereof. Preferably, the polysaccharide solution comprises dextran. The dextran may have an average molecular weight of, for example, between 5,000 Da and 110,000 Da.

The polysaccharide solution may be at a variety of concentrations. For example, the polysaccharide solution may comprise between about 0.5% and about 20% weight/volume. Furthermore, the polysaccharide solution may be at pH of, for example, between about 5 and about 11.5.

The magnetic crystals may be combined with the polysaccharide solution in a variety of ways. For example, the mixture of magnetic crystals and the polysaccharide solution may be combined by flow-mixing, as described hereinabove. Alternately, the magnetic crystals and the polysaccharide solution may be added to a vessel, and mixed, either manually or automatically.

In some embodiments, the magnetic crystals are combined with the polysaccharide solution at high temperatures, and subsequently allowed to cool. For example, the polysaccharide may be between about 20° C. and about 95° C. when combined with the magnetic crystals. Preferably, the polysaccharide solution is at about 85° C. when combined with the magnetic crystals.

After being combined, the magnetic crystals and the polysaccharide solution may be allowed to incubate for a period of time. For example, the magnetic crystals and the polysaccharide solution may be allowed to incubate for between 1 hour and 7 hours.

Without being limited by theory, it is believed that when the magnetic crystals are combined with the polysaccharide solution, the polysaccharides are adsorbed to the metal surface and may fully or partially coat the metal oxide crystal surface. The coated crystals then aggregate to form magnetic particles which comprise a matrix of polysaccharide and a plurality of magnetic crystals dispersed in the matrix. The magnetic particles may also be described as an aggregate of polysaccharide coated magnetic crystals.

The magnetic crystals may comprise between about 60 wt % and about 85 wt % of the particles. More specifically, the crystals may comprise between 75 wt % and 83 wt % of the particle.

In some embodiments, the magnetic particles initially formed by combining the magnetic particles and the polysaccharide solution may be large agglomerates with diameters ranging from 0.5-400 microns. Accordingly, in some such embodiments, the method may further comprise reducing the diameter of the particles.

The diameter of the particles may be reduced in a variety of ways. In some embodiments, the diameter is reduced to between about 0.5 microns and 10 microns by disaggregation. More particularly, the diameter may be reduced to between 0.9 and 2.5 microns. For example, microfluidization may be used to reduce the diameter of the particles. In such embodiments, an external air compressor may be used to force the particles through one or more chambers containing a chamber of a defined size. Alternately, extrusion may be used to reduce the diameter of the particles. In such embodiments, the particles may be forced under gas pressure or through positive displacement through pores of a defined size in a membrane.

Optionally, after the particles are formed, they may be washed to remove unbound polysaccharide, magnetic particles with lower magnetization and/or remaining dissolved metals. Further, they may be washed to reduce the pH of the suspension. For example, the pH may be reduced to about 7. The particles may be washed by, for example, centrifugal washing, magnetic washing, and/or tangential filtration. Preferably, the wash is carried out at between 17 and 25° C. The particles may be washed with water or with a buffered salt solution.

The magnetic particles may be used according to a variety of methods for magnetically separating cells. For example, in embodiments wherein it is desired to separate a first population of cells from a second population of cells, the magnetic particles may be linked to a first population of cells. The magnetic particles may be linked to a first population of cells, for example, by using tetrameric antibody complexes. The mixture of cells may then be placed in a magnetic field and, and the desired population of cells may be recovered. In embodiments wherein the particles have a large diameter, for example of >1 microns, the separation time may be relatively low, for example less than 2 minutes, and a relatively weak magnetic field may be used, for example less than 20 T/m.

In some embodiments, it may be desirable to analyze the first population of cells by FACS. In such embodiments, the shift in the side scatter signal of the cells may be less than about 100% as detected by flow cytometry.

It will be appreciated that certain features of the, which are, for clarity, described in the context of separate embodiments or separate aspects, may also be provided in combination in a single embodiment. Conversely, various features, which are, for brevity, described in the context of a single embodiment or aspect, may also be provided separately or in any suitable sub-combination.

Although the description has been made in conjunction with specific embodiments thereof, if is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention.

EXAMPLES

Example 1

Particle Synthesis

Magnetic particles were prepared according to the novel process outlined below.
Preparation of Iron Solution and Base Solution Iron solutions were prepared in $N_2$ sparged de-ionized water using iron (II) chloride tetrahydrate and iron (III) chloride hexahydrate at approximately a 1:2/$Fe^{2+}$:$Fe^{3+}$ molar ratio. This solution was sparged with $N_2$ prior to use. The reagents were stored with head-space clearing using $N_2$ to prevent oxidation.

Base solutions were prepared using $NH_4OH$ solutions diluted in previously $N_2$ sparged de-ionized water or using NaOH in previously $N_2$ sparged de-ionized water.
Crystallization The base solution was added to the iron solution by means of flow mixing. Peristaltic pumps (Dynamax Model RP-1) were used to combine the iron and base solutions at a controlled volumetric ratio. The base and iron solutions were pumped independently through Tygon tubing (Cole-Parmer) to a Y or T junction where they mixed and reacted as the combined solutions flowed away from the junction through a third length of tubing. The crystallization reaction proceeded as the mixture flowed though this third length of tubing and led to the formation of magnetic crystals. The flow mixing crystallization step was performed at temperatures up to 70° C. Crystals were formed at all temperatures tested (from room temperature to 70° C.); however the iron solution became cloudy when heated above 50° C.
Crystal Coating The product of the crystallization reaction was combined with a dextran solution and maintained at high temperature (~85° C.) for a given period of time and then allowed to cool. They were combined as above using flow mixing, or by addition to a vessel containing the dextran solution. This dextran solution was prepared by disolving USP quality dextran with an average molecular weight of between 5,000 and 110,000 Daltons in $N_2$ sparged de-ionized water at a final concentration between 0.5% and 20% weight/volume. The dextran solution volume was in the range of 0.2 to 4 times the volume of the mixture formed in step 2.
De-aggregation The particles initially presented as large agglomerations with diameters ranging from 3-400 um and population mean diameters between 12 and 100 µm. The particles were disaggregated by sonication, microfluidization or extrusion. In cases of sonication, the particles were sonicated for a certain period of time between 1 to 60 minutes to achieve the desired mean size distribution. In cases where microfluidization was used, an external air compressor forced the particles through one or multiple chambers containing a defined size channel. The combination of chamber design and pressure determined the final particle size. Disaggregation by extrusion was achieved by forcing the particles through pores of a defined size in a membrane. Extrusion was performed under gas pressure or through positive displacement. Where pressure-based extrusion was used, compressed $N_2$ gas was chosen.
Wash Washing was performed to remove unbound dextran, particles with lower magnetization, remaining dissolved iron and to reduce the pH of the suspension to around 7. Washing was done in one of three ways. For centrifugal washing, the suspension was centrifuged at an average 1000×g for 30 min, the supernatant was removed and the particles were resuspended. This sequence was repeated as required. For magnetic washing, the magnetic material was separated in a magnetic field, the supernatant was removed and the particles were resuspended. This sequence was repeated as required. The third method involved washing by tangential filtration with a volume several fold that of the input material and a membrane with a 0.05 µm pore size and surface area of 3100 $cm^2$. In all cases, washing was done with de-ionized water. The optimal temperature for washing the extruded particles was between 17-25° C. Higher temperatures were undesirable due to the potential for re-aggregation. Each wash method was performed with at least 2 volume changes and sometimes more than 5 volume changes.

Example 2

Cell Separation

Cell separation using the particles prepared as in Example 1 was performed using EasySep reagents from Stemcell Technologies Inc. For positive selection of human cells, a single cell suspension was labeled with tetrametic antibody complexes (TAC) which consisted of antibodies against a cell surface marker linked to an anti-dextran antibody. For negative selection, the cells were labeled with a cocktail of TAC that target unwanted cells. Following incubation of the cells with TACs, magnetic particles were added to the cell suspension and incubated to allow binding of the particles to the cells via the anti-dextran antibody on the TACs.

The cell suspension was then diluted to a given volume and placed in a magnet. Cells labeled with particles moved to the sides of the tube due to the magnetic field gradient. The unlabeled cells were removed with the supernatant. The targeted labeled cells were collected once the magnetic field was removed. Particles were used to either positively or negatively select human cell types from various cell sources.

The particle concentration was measured using either optical density (OD) or measuring the dry mass of the particles. OD was used as a surrogate measure of particle concentration. The stock particle OD was calculated from the OD of a known dilution having an OD between 0.3 and 2.0 measured using a spectrophotometer. The OD used for cell separation was based on the effective final OD in the sample based on the dilution of the stock in the sample. For positive selection experiments using the particles prepared as in Example 1, the typical particle concentration ranged from OD 0.5 to OD 6. For negative selection, the typical particle concentration ranged from OD 1 to OD 24. Dry mass was used as a measure of particle concentration. The dry mass used for cell separation was based on the measured dry mass after dilution of the stock sample. For positive selection experiments using the particles prepared as in Example 1, the typical particle concentration ranged from 0.05 to 0.6 mg. For negative selection, the typical particle concentration ranged from 0.1 to 2.4 mg.

Human cell types that were positively selected from Peripheral Blood Mononuclear Cells (PBMC) include $CD3^+$ (STEMCELL Technologies Cat# 18051), $CD4^+$ (Cat# 18052), $CD33^+$ (Cat# 18527), $CD19^+$ (18054), and $CD34^+$ (Cat# 18056). Human cell types that were positively selected from whole blood include $CD3^+$ (Cat# 18081), $CD15^+$ (Cat# 18681) $CD19^+$ (Cat# 18084), and $CD33^+$ (Cat# 18287). Human cell types that were negatively selected from PBMC include $CD3^+$ T Cells (Cat# 19051), $CD4^+$ T Cells (Cat# 19052), $CD4^+$Naïve T Cells (Cat#

19155), CD4+ Memory T Cells (Cat# 19157), CD8+ T Cells (Cat# 19053), CD19+ B Cells (Cat# 19054 and 19154), CD56+NK Cells (Cat# 19055), CD14+CD16− Monocytes (Cat# 19059), CD14+CD16+Monocytes (Cat# 19058), pan Dendritic Cells (Cat# 19251), Eosinophils (Cat# 19256), Basophils (Cat# 19069), Neutrophils (Cat# 19257), CD34+ Hematopoetic Progenitors (Cat# 19056 and 19057). Human cell types that were negative selected from HetaSep™ treated whole blood include CD3+ and CD19+ Total Lymphocyte (Cat# 19961HLA), CD3+ T Cells (Cat# 19951HLA), and CD19+ B Cells (Cat# 19054HLA).

Mouse splenocytes or bone marrow cells were labeled first with conjugated antibodies, then by TAC which consist of antibodies against the conjugate linked to an anti-dextran antibody and finally with dextran-coated particles. In the present example, biotin was used as the conjugate. Mouse cells types that were negatively selected from spleenocyte preparations include CD3+ T Cells (Cat# 19751), CD4+ T Cells (Cat# 19752 and 19772), CD8+ T Cells (Cat# 19753), and B Cells (Cat# 19754). CD34+ Hematopoetic Progenitors (Cat# 19756) were negatively selected from bone marrow preparations and Mesenchymal Progenitors (Cat# 19771) were negatively selected from compact bone preparations.

When hematopoetic progenitors were selected (by either positive or negative selection) from both human and mouse cell sources, MethoCult® Colony Forming Cell Assays (Stemcell Technologies) showed that cells selected by particles described herein had healthy and typical morphology as compared to cells selected using EasySep® Nanoparticles (Cat# 18150) and compared to cells that had not undergone immunomagnetic selection.

Purity of the desired cells was determined by flow cytometry using fluorescently-labeled antibodies appropriate for the desired cell type. Recovery of the desired cells was calculated from the number of cells of the desired type present in the initial and enriched sample. The recovery was calculated as the number of desired cells in the enriched sample divided by the number of desired cells in the initial sample. The number of desired cells in the initial and enriched sample were determined by multiplying the total number of cells in the sample (determined from the sample volume and cell concentration) by the desired cell concentration (determined by flow cytometry). The cell concentration was determined using a hemocytometer.

Example 3

Particle Size and Morphology

Particle sizes of particles formed as described in Example 1 were evaluated using multi-angle light scatter (Horiba LA-950 instrument) following the manufacturer's recommended sample preparation procedures. Particle sizes from 0.2 to 30 μm mean diameter were measured routinely.

Particles were examined by brightfield microscopy for morphological characteristics. Microscopic visualization of particles prior to extrusion showed irregular aggregates of crystallized magnetic material surrounded by a dextran matrix. After extrusion the particles appeared spherical or rod-like.

Example 4

Effect of Process Variables on Particle Formation

Iron solution concentrations are reported as total soluble iron concentration for solutions made with Iron(II) Chloride Tetrahydrate and Iron (III) Chloride hexahydrate prepared at a 1:2 molar ratio for Fe(II) to Fe(III). [e.g. 32 mM solution would be 10.7 mM Fe(II) and 21.3 mM Fe(III)]. Iron solution concentrations between 8 mM and 385 mM were tested. Particles produced with an iron solution below 8 mM did not persist: evidence of particle formation based on change in the color of the solution from brown to black was only transient, with the solution returning to light brown within a minute. Using an iron concentration of 1 mM resulted in no visible particle formation. Iron solution concentrations higher than about 150 mM yielded very large, sticky aggregates that were impractical to work with.

NH$_4$OH solution concentrations from 1% to 30% were evaluated. The target minimum pH of the base/iron mixture was 10.5, based on pH studies that showed crystal formation was impaired at pH values lower than this. Using a 32 mM iron solution and a 1:1 iron:base volumetric flow ratio in the flow mixing device, this target pH was attained by using a 6% base solution concentration. A base solution concentration of 3% was slightly below this target while 1% was drastically lower. Base concentrations higher than 6% did not noticeably improve particle formation.

The iron (32 mM) and base solutions (6% to 30% NH$_4$OH) were combined in the flow mixing process at different volumetric ratios. Ratios of 5:1, 3:1, 2:1 and 1:1 iron solution:NH$_4$OH generated particles that performed equivalently in cell separation as long as the final pH was above 10. Manipulating the flow ratios has a similar effect to manipulating the solution concentrations.

The effect of incubation time for the iron and base solution mixture (prior to dextran addition) was evaluated in the range from 0 s to several hours (batch mixing). Residence times were modified by varying the tubing length (1 to 30 cm lengths were used) and varying the tubing diameter (0.3 to 2 cm diameters used). For batch incubation, a separate reservoir (1 mL to 30 mL volumes) with or without agitation was used. A short residence time (≤5 seconds) post-mixing was found to be the most desirable. An extended residence time (30-180 seconds) created larger particle aggregates (up to 20 microns diameter), which are not desirable for cell separation but may have utility for dense particle applications.

Following combining the magnetic crystals with dextran, an extrusion step was performed to de-aggregate particles and ensure a uniform size distribution. The optimal temperature for extrusion was found to be about room temperature (about 20-25° C.). Higher temperatures (>40° C.) were undesirable due to the potential for re-aggregation. Flux rates down to 0.01 mL/min/cm$^2$ and up to 50 mL/min/cm$^2$ were tested. The optimal flux rate for extrusion was about 0.5 mL/min/cm$^2$. Lower flux rates resulted in lengthy processing times. Higher flux rates resulted in a small mean particle size and poor cell separation performance.

De-aggregation of particles by microfluidization was successful but lacked suitable control to make the process as robust as extrusion. To achieve the desired particle size, the microfluidizer was operated at the lowest end of the pressure range.

Example 5

Cell Separation: Effect of Iron and Base Solution Concentration During Synthesis Particles were prepared as described in Example 1 using either NH$_4$OH or NaOH during the crystallization step. A 32 mM iron solution was flow mixed with either NH$_4$OH or NaOH and the resulting crystals were added to a 15% w/v T-40 dextran solution at ~85° C. 1%, 6%, and 30% NH$_4$OH solutions and 0.2M and 1.0 M NaOH solutions were investigated.

Results for CD19+ cell separation using the resulting particles are shown in Table 1. Particles synthesized with 30% NH$_4$OH mixed at 1:1 and 0.2M NaOH mixed at 1:1 both had a comparable final pH>11, but the particles made with NaOH gave a lower recovery of CD19+ cells after cell separation. This suggests that the difference in performance between the two bases is not due to differences in final pH (previous experiments demonstrated consistent particle synthesis at a >pH 10 using NH$_4$OH), but to some other difference in the way the particles are formed.

TABLE 1

Effect of base type on particle performance in cell separation CD19$^+$ cells were positively selected from previously frozen PBMC.

| Iron Solution: Base Solution Volume Ratio | Type of Base Solution | Base Solution Concentration | pH of Combined Iron and Base Solutions | % Purity | % Recovery |
| --- | --- | --- | --- | --- | --- |
| 5:1 | NH4OH | 1% | 5 | 19.00 | 0.02 |
| 1:1 | NH4OH | 1% | 9.83 | 96.00 | 33.00 |
| 5:1 | NaOH | 1.0 M | 11.68 | 98.00 | 32.00 |
| 1:1 | NaOH | 1.0 M | 12.69 | 94.00 | 28.00 |
| 1:1 | NH4OH | 30% | 11.29 | 99.00 | 59.00 |
| 5:1 | NH4OH | 30% | 10.68 | 93.00 | 58.00 |
| 1:1 | NaOH | 0.2 M | 11.45 | 98.00 | 43.00 |
| 5:1 | NH4OH | 6% | 9.86 | 98.00 | 41.00 |
| 1:1 | NH4OH | 6% | 10.62 | 99.00 | 71.00 |
| Standard EasySep ® Nanoparticles | | | | 99.00 | 68.00 |

Example 6

Cell Separation: Effect of Fe(II):Fe(III) ratio

The effect of Fe(II):Fe(III) was tested by making particles using a batch method and flow cell method for the crystallization step as described in Example 1 and then performing a NK negative selection from human PBMC as described in Example 2. The results in Table 2 show that the batch synthesis method produces particles that are not as useful for cell separation as the flow mixing method. In addition, the results show that increasing the amount of each iron component by 25% or 100% will still result in formation of particles, however the addition of increased amount of Fe(II) or Fe(III) leads to lower particle yields and particles with poor performance in cell separation applications.

TABLE 2

Effect of iron concentration on cell separation performance NK Cells were negatively selected from previously frozen PBMC. Purity is analyzed as CD56$^+$CD3$^-$. Recovery is calculated from cell counts using a haemacytometer.

| % NH$_4$OH | Fe solution as described in Example 1 | Mixing | Mixing time (min) | % Purity | % Recovery |
| --- | --- | --- | --- | --- | --- |
| 6 | 1:2 | Batch | 2 | 23 | 69 |
|   |     |       | 60 | 18 | 100 |
|   | 1.25:2 |    | 2  | 20 | 85 |
|   |     |       | 60 | 19 | 65 |
|   | 1:1 |       | 2  | 70 | 75 |
|   |     |       | 60 | 26 | 81 |
|   | 1:2.5 |     | 2  | 22 | 98 |
|   |     |       | 60 | ND | ND |
|   | 1:4 |       | 2  | 9  | 6  |
|   |     |       | 60 | ND | ND |
|   | 1:1.8 | Flow Mixing | — | 86 | 96 |
|   | 1:2 |       | —  | 97 | 72 |
|   | 1:2.1 |     | —  | 88 | 80 |
|   | 1:2.2 |     | —  | 77 | 105 |

Example 7

Cell Separation: Effect of Dextran Solution Concentration and pH

Dextran solutions were prepared at concentrations from 0.5% up to 20% w/v in water as described in Example 1. Solutions of greater than 20% w/v dextran were not practical due to increasing difficulty in solubilizing the dextran. The pH of the dextran solution was adjusted to between pH 5 and pH 11 using NH$_4$OH. Particles produced using these dextran solutions were used in cell separations as described in Example 2. Data in Table 3 for CD19+ selection show that using higher pH dextran solutions during particle synthesis results in particles that give higher purity and recovery when used in cell separation. It appears that a pH of 10.6 for the dextran solution is better than pH 11.3. Table 4 shows NK cell negative selection results using particles produced with dextran solutions at different dextran concentration and pH, with and without sparging during the coating step. The data in this table confirm that a high pH dextran solution is important for purity and recovery and that nitrogen sparging during the coating step results in lower purity, regardless of dextran concentration. The best cell separation results were obtained for particles produced using a 15% w/v dextran solution at pH 10 to 10.6. Magnetic particles prepared below 3% w/v of dextran resulted in uncontrolled aggregation of the particles where the mean particle size is greater than 5 µm. These larger aggregates with less dextran used in the coating process also results in poorer cell separation performance. Due to this result, it is believed that the dextran is essential to the passivation of the particle surface, preventing particle aggregation and modifying cell separation performance.

TABLE 3

Effect of adsorption pH on cell separation performance CD19$^+$ cells were positively selected from previously frozen PBMC.

| % Dextran | Adsorption pH | % Purity | % Recovery |
| --- | --- | --- | --- |
| 15 | 5 | 19 | 0.02 |
| 15 | 9.8 | 96 | 33 |
| 15 | 10.6 | 99 | 71 |
| 15 | 11.3 | 99 | 59 |

TABLE 4

Effect % dextran, adsorption pH, and agitation during adsorption on cell separation performance
NK Cells were negatively selected from previously frozen PBMC.
Purity is analyzed as CD56+CD3− using flow cytometry.

| % Dextran | Adsorption pH | $N_2$ sparging | % Purity | % Recovery |
|---|---|---|---|---|
| 15 | 10 | yes | 60 | 73 |
| 0.5 | 10 | yes | 11 | 100 |
| 15 | 10 | no | 89 | 94 |
| 0.5 | 10 | no | 24 | 82 |
| 15 | 8 | yes | 9 | 46 |
| 0.5 | 8 | no | 17 | 65 |
| 5 | 10.6 | no | 75 | 89 |
| 10 | 10.6 | no | 83 | 89 |
| 15 | 10.6 | no | 97 | 72 |
| 20 | 10.6 | no | 73 | 102 |

Example 8

Cell Separation: Effect of Dextran Solution Temperature and Incubation Time

The temperature of the dextran solution used in Example 1 was varied between 20° C. and 90° C. The particles produced were then tested in CD19+ cell separation as described in Example 2. As seen in Table 5, the recovery of the targeted cell population in positive selection was significantly higher using particles produced with the dextran solution at 70° C. than when the dextran solution is at 20° C. This is likely due to the superior binding of the dextran to the crystal surface that occurs at higher temperatures (Bautista, Bomati-Miguel et al.). This improved recovery was observed for dextran solutions made with both 10 kDa and 40 kDa dextran. Table 6 shows that increasing the incubation time for the step of combining the crystals with the polysaccharide solution from 2 hours to 7 hours had no significant effect on cell separation results for both 10 kDa and 40 kDa dextran. No detrimental effect on cell separation performance was seen with heated adsorption times as low as 1 hour.

TABLE 5

Effect of adsorption temperature on cell separation performance
CD19+ cells were positively selected from previously frozen PBMC.

| Dextran Type | Adsorption Conditions | % Purity | % Recovery |
|---|---|---|---|
| 10 kDa | 2 h @ ~20° C. | 99 | 19 |
| 10 kDa | 2 h @ >70° C. | 99 | 42 |
| 40 kDa | 2 h @ ~20° C. | 98 | 26 |
| 40 kDa | 2 h @ >70° C. | 99 | 40 |

TABLE 6

Effect of adsorption time on cell separation performance
CD19+ cells were positively selected from previously frozen PBMC.

| Dextran Type | Adsorption Condition | % Purity | % Recovery |
|---|---|---|---|
| 10 kDa | 2 h @ >70° C. | 97 | 27 |
| 10 kDa | 7 h @ >70° C. | 99 | 31 |
| 40 kDa | 2 h @ >70° C. | 99 | 36 |
| 40 kDa | 7 h @ >70° C. | 99 | 26 |

Example 9

Cell Separation: Effect of Additives

The effect of adding various excipients during the adsorption process, including 5M NaCl), 85% ethanol, 10% Tween-20 surfactant was investigated. 20% of the final volume during adsorption consisted of the additive solution. As seen in Table 7, the best cell separation performance was observed with particles adsorbed without the addition of any of these excipients.

Different excipients were added to the dextran solution, including salt (5M NaCl), alcohol (85% ethanol) and surfactant (10% Tween-20). 20% of the final volume consisted of the additive solution. The data in Table 7 show that the particles prepared using a volume control in place of the excipient gave improved performance in negative selection of NK cells from previously frozen human PBMC than the particles prepared with the excipients.

TABLE 7

Effect of excipients added during adsorption on cell separation performance
NK Cells were negatively selected from previously frozen PBMC.

| Additive | % Purity | % Recovery |
|---|---|---|
| Volume control | 87 | 100 |
| 5M NaCl | 53 | 100 |
| 85% EtOH | 44 | 27 |
| Tween-20 | 83 | 67 |

Example 10

Cell Separation: Effect of Particle Size and Method Used for Determining Particle Concentration A range of particle sizes from ~1.8 microns–~18 microns manufactured by the process described in Example 1 using extrusion membranes to disaggregate the particles. Particle size was measured with a Horiba LA-950 that uses multi-angle light scatter and two different lasers to determine particle size. The particles were extruded through different combinations of polycarbonate track etch membranes manufactured with 5 microns, 3 microns and 2 microns pore sizes as shown in Table 8. The final OD (particle concentration) of the particles after addition to the cell suspension was 6.0. Table 8 shows that cell separation performance (NK negative selection) where the particle concentration is measured using OD was independent of particle size. Larger particles tended to settle faster and thus the preferred diameter is ~2 microns.

A range of particle sizes from ~1.0 microns–~3.1 microns was manufactured by the process described in Example 1 using extrusion membranes to disaggregate the particles. Particle size was measured with a Horiba LA-950. The particles were extruded through a polycarbonate track etch membranes with 5 microns, 3 microns and 2 microns pore sizes. A dry mass of 0.6 mg of particle was added to each 1.0 ml of cell suspension (0.6 mg/ml) to ensure a consistent amount of particles. Table 9 shows that cell separation performance (NK negative selection) is dependent on particle size where a larger average particle diameter results in lower purities. The lower purities can be remedied by adding 50% more particles (ie. 0.9 mg/ml) in the cell separation. These data suggest that cell separation performance is dependent on the particle surface area present for the attachment of TAC for cell separation. Since the same concentration of particles was added to all the cell separations, larger particles would have a lower surface area for attachment of TAC, resulting in lower cell purities. Addition of more particles remedies this problem by increasing the total surface area present and giving larger particles the same performance as smaller particles at a lower concentration. Particles with diameters below about 1 micron result in lower cell recovery, with recovery lower than 40% for 0.6 micron diameter particles. This suggests that the increased surface area at smaller diameters also increases non-specific binding to the cells. Therefore, there appears to be optimum average particle diameter between 1.0 and 2.5 µm where the highest purities and recoveries are achieved in cell separation.

The dry mass and OD of a few different samples were measured to determine if there is a direct correlation between the two measurements of concentration used for cell separation. It appears from Table 10 that there is a loose correlation between the two measurements. However, particles with the highest dry mass do not correspond to particles with the highest OD. This is possibly due to the variation in size between the different samples. According to Mie theory, larger particles (mean=3 µm) will have a larger amount of forward scattered light compared to smaller particles (mean=1 µm) which will result in a higher level of transmitted light and lower values for absorbance or OD compared to smaller particles at the same dry mass concentration. This explains the data in Table 9 where no difference in cell separation performance is seen using OD as a measurement for particle concentration. This is because the larger particles (mean=18 µm) physically requires more particles present in solution to achieve the same OD and more particles would improve the cell separation performance that was affected detrimentally by having a larger particle size.

TABLE 8

Effect of particle size on cell separation performance (OD)
NK Cells were negatively selected from previously frozen PBMC.

| Particle | Mode Size (um) | Median Size (um) | Standard Deviation of Median (um) | % Purity | % Recovery |
|---|---|---|---|---|---|
| Start Material | 17.5 | 14.5 | 3.6 | 83 | 54 |
| Extruded through 5 um membrane | 4.8 | 4.3 | 2 | 81 | 60 |
| Extruded through 5 um then 3 um membranes | 2.4 | 2.4 | 1.5 | 83 | 51 |
| Extruded through 5 um, 3 um, then 2 um membranes | 1.6 | 1.8 | 1.6 | 84 | 50 |
| EasySep ® Microparticles | 1.4 | 1.6 | 1.0 | 80 | 52 |

TABLE 9

Effect of particle size on cell separation performance (dry mass)
NK Cells were negatively selected from previously frozen PBMC.

| Particle | Mode Size (um) | Median Size (um) | Standard Deviation of Median (um) | % Purity | % Recovery |
|---|---|---|---|---|---|
| Extruded through 5 um, then 3 um membranes | 1.1 | 1.0 | 0.5 | 92 | 62 |
| | 1.5 | 1.3 | 0.7 | 91 | 67 |
| | 2.6 | 2.3 | 1.2 | 80 | 72 |
| | 3.1 | 2.8 | 1.4 | 85 | 68 |

TABLE 10

Relationship between OD and dry mass

| OD | Dry mass (mg/ml) | Average diameter (microns) |
|---|---|---|
| 58.2 | 5.8 | 1.10 |
| 56.3 | 6.4 | 2.59 |
| 57.9 | 6.7 | 3.07 |
| 60.6 | 6.3 | 2.82 |
| 59.1 | 5.9 | 1.48 |
| 60.1 | 6.7 | 2.35 |
| 60.7 | 5.8 | 1.11 |

Example 11

Cell Separation: Comparison with EasySep® Microparticles and Nanoparticles—Effect of Particles on Light Scatter in Flow Cytometry The particles produced as described in Example 1 were used in EasySep® CD3 Positive Selection from fresh blood. As a control CD3 cells were selected with EasySep® Microparticles (Cat# 19250). The mean diameter for the particles described herein was 1.1 µm, while the mean diameter for the EasySep® Microparticles was about 1.0 µm. FIG. 1 shows flow cytometry plots for the enriched cells. Panels A and B show that the CD3+ cell purity was comparable for cells selected with the particles described herein and EasySep® microparticles cells. The recovery of CD3+ cells was also comparable. However, the side scatter signal of the cells selected with the magnetic particles described herein (panel D) was much lower than that for the cells selected with the EasySep® microparticles (Panel C). In fact, the light scatter signal for the cells selected with the particles described herein were essentially the same as the signal for the unselected cells. This shows that the particles described herein have a significant advantage over the EasySep® microparticles for positive selection, in that the light scatter signal in flow cytometry of the selected cells is essentially equivalent to the signal of the desired cells prior to selection.

Cells positively selected using the particles described herein, did not exhibit significant side-scatter shift upon FACS analysis. In comparison, cells selected with similar sized EasySep® Microparticles exhibited a shift in the side scatter profile. Particles of similar diameter from other suppliers also caused a significant side-scatter shift. CD3 positive selection from fresh whole blood was performed using the particles described herein with EasySep® Microparticles, Dynal and Merck microparticles coated with a dextran, and EasySep® Nanoparticles. Table 11 shows the diameters for the particles as well as the purity of the positively selected cells and the mean forward and side scatter signals for the positive cells obtained during flow cytometric analysis. The results show that while the purity of the target cells is comparable after cell separation, the effect on side scatter (SSC) is a strong function of the type of particle used. The CD3+ cells selected with the particles described herein had mean SSC signal of 65. Cells selected using the other particles of similar diameter (range 1.1 to 2.5 μm) had a mean SSC signal between around 130 and 200.

TABLE 11

Side Scatter Shifts of various particle types

| Description | Particle size ± Standard Deviation (um) | Purity of CD3+ cells (%) | FSC Mean channel intensity | SSC Mean channel intensity |
|---|---|---|---|---|
| Start Sample | N/A | 58 | 73 | 27 |
| EasySep ® Nanoparticles | 0.25 ± 0.15 | 88 | 87 | 44 |
| EasySep ® Microparticles | 1.3 ± 0.5 | 90 | 90 | 129 |
| Particles Described herein | 1.7 ± 1.0 | 83 | 99 | 65 |
| Merck Microparticles | 2.5 | 90 | 90 | 148 |
| Dynal Microparticles | 1.1 | 86 | 83 | 203 |

The lack of side scatter shift for cell separated using the particles described herein was observed over a wide range of particle sizes. Various particle sizes were obtained by extrusion and the resultant particles were used to positively select the CD4+ population from fresh whole blood. The CD4+ T Cell population was detected as CD45+CD14−CD4+ in flow cytometry and the CD4+Monocyte population was detected as CD45+CD14+. Both populations showed a significant SSC shift with EasySep® Microparticles but not with the particles described herein regardless of particle diameter. The results for these experiments are summarized in Table 12.

The effects of concentration and molecular weight of dextran used in preparation of the particle described herein were also investigated. The particles produced as described in Example 1 were used in EasySep® CD3 positive selection from frozen PBMCs. As a control CD3 cells were selected with EasySep® nanoparticles (Cat# 19250). Particles were prepared according to Example 1 using different dextran solution concentrations and dextran molecular weight. The data from Table 13 show that the side scatter (SSC) shift for cells separated using the particles described herein relative to the SSC shift for cells separated with nanoparticles $[(SSC_{particles} - SSC_{NanoParticles})/SSC_{NanoParticles}]$ is independent of dextran concentration during synthesis. This is possibly because dextran is in excess at concentrations as low as 5 w/v %. Lower concentrations of dextran (3 and 1 w/v %) were also tested but the particles synthesized formed large clumps, suggesting that not enough dextran was present to passivate the particle surface and prevent aggregation.

Dextrans of different molecular weights were used to look for an effect on the amount of dextran in the particles. The hypothesis was that similar number of dextran molecules would coat the particles but a lower molecular weight would lead to a lower weight % of dextran in coated particles. The lower weight % of dextran in the particles would lead to a lower effective refractive index and less side scatter according to Mie theory. This phenomenon is observed for the 5 kDa dextran sample compared to 40 KDa sample (Table 13) where lower weight percentage of dextran leads to increased side scatter shift. For particles where 110 kDa is used, the % side scatter shift does not decrease. One possible explanation is that higher molecular weight dextran molecules have steric effects that prevent them from packing efficiently around the particles leading to a mass % of dextran comparable to the 40 kDa sample and hence a similar side scatter profile.

TABLE 12

Side Scatter Shift of various particle sizes

| Sample | Description | Purity of CD4+ cells (%) | Particle size (μm) | Mean channel intensity (FSC) | Mean channel intensity (SSC) |
|---|---|---|---|---|---|
| A | Start | 17.8 | N/A | 92 | 37 |
| B | Post-adsorption, no extrusion | 99.3 | 18 ± 11 | 90 | 37 |
| C | 5 μm high pressure extrusion | 99.1 | 3.8 ± 1.8 | 94 | 64 |
| D | 5 μm/3 μm high pressure extrusion | 98.4 | 2.3 ± 1.8 | 95 | 68 |
| E | 5 μm/3 μm/3 μm high pressure extrusion | 98.0 | 1.5 ± 1.0 | 93 | 67 |
| F | 5 μm/3 μm/3 μm low pressure extrusion | 99.0 | 2.3 ± 1.4 | 92 | 53 |
| G | EasySep ® Microparticles | 99.6 | 2.4 ± 1.4 | 96 | 245 |
| H | EasySep ® Nanoparticles | 97.5 | 0.10 ± 0.01 | 86 | 50 |

TABLE 13

Side Scatter Shift as a function of dextran concentration and dextran MW

| Sample | Molecular weight (kDa) | w/v % of dextran used in synthesis | % Side Scatter shift relative to EasySep nanoparticles |
|---|---|---|---|
| A | 40 | 5 | −3.0 |
| B | 40 | 10 | −6.8 |
| C | 40 | 15 | −5.0 |
| D | 40 | 20 | −6.9 |
| E | 5 | 15 | 3.7 |
| F | 110 | 15 | −3.0 |

The variation of the dextran molecular weight had an effect on the average particle size that was prepared. Sample E (Table 13) synthesized with 5 kDa dextran had the smallest average particle diameters prior to extrusion where the size measured by light scattering was 2.0 microns. Increasing the molecular weight of dextran increases the size of the particles. Particles synthesized with dextran with molecular weights of 40 and 110 kDa had average diameters of 6.3 microns and 21.5 microns, respectively, when measured immediately after synthesis. The size of the particles had effects on the yield of the particles. Since most of the particles with 5 kDa dextran were smaller, they were less magnetic and were removed during the magnetic washing step. The particles made with 110 kDa were much larger and contained large clusters that were filtered out during extrusion. The 40 kDa particles had the optimum size for extrusion and also resulted in the best yield.

Figure 2:
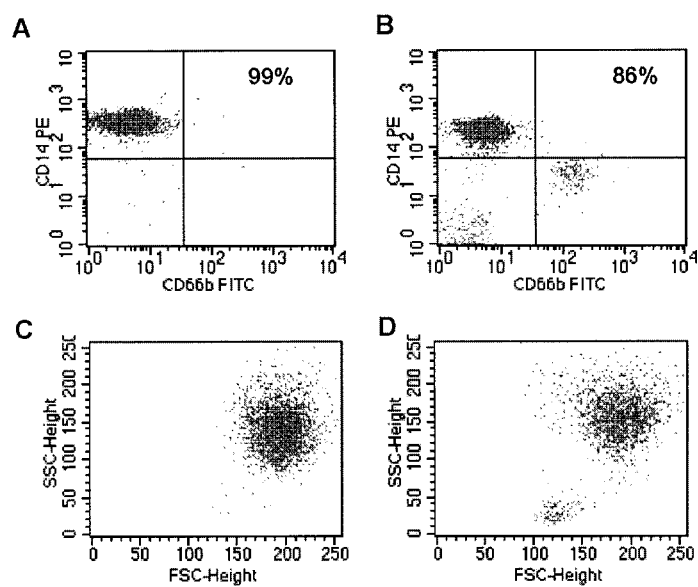
FIG. 2 is a graph showing side scatter properties of cells purified by CD14 positive selection using the particles described herein compared to EasySep® Nanoparticles. Panels A, B are representative FACS plots of cells following CD14 positive selection analysed for expression of CD66b and CD14 antigens. Panels C, D are representative FACS plots of the forward vs. side scatter profile of CD14 selected cells. Panels A and C depict cells selected with EasySep® Nanoparticles. Panels B and D depict cells selected with Particles described herein.

The particles described herein were used in EasySep® CD14 Positive Selection protocol as described in Example 2 using fresh blood (washed buffy coat). The recovery of CD14+ cells using the particles described herein (65%) was significantly higher than the control sample separated with EasySep® Nanoparticles (12%). The purity of the enriched sample was higher for the cells selected using EasySep® Nanoparticles. This was likely due to non-specific binding from the particles described herein that was caused by the high particle concentration. Despite the likely excess particle concentration, the SSC signal for the cells selected with the particles described herein was equivalent to that for the EasySep® Nanoparticles. This is show in FIG. 2.

The particles described herein, EasySep microparticles and EasySep nanoparticles were used in EasySep® CD4 positive Selection protocol as described in Example 2 using fresh blood (washed buffy coat). The recovered CD4+ cells using the three different particles were analyzed using Multispectral Imaging Flow Cytometry (Amnis ImageStream) which allows the visualization of individual cells (microscopy) combined with flow cytometry. The particles disclosed herein were significantly less visible on the surface of the cell compared to the EasySep Microparticles using Brightfield image analysis even though both particles are comparable in size (diameter≈1 microns). The visibility on the surface of the cell of the particles described herein was comparable to EasySep nanoparticles which are much smaller in size (~250 nm). Furthermore, cells positively selected using the particles described herein exhibited the least side-scatter profile compared to the other two particles.

Example 12

Alternate Particle Surfaces

The dextran coating on the particles was oxidized with a mild oxidizing agent such as sodium metaperiodate in sodium acetate buffer. This result in the oxidation of carbohydrate moieties to aldehyde groups. Prolonging the reaction resulted in oxidation of aldehyde groups to carboxyl groups.

Particles were prepared as outlined in Example 1 and resuspended 0.1M sodium phosphate buffer at pH 7.2. 20 mM sodium meta-periodate was prepared in 0.1 M sodium acetate buffer at pH 5.5. Equal volumes of particle suspension and sodium meta-periodate solution were mixed in a light-protected vessel at 2-8° C. for 30 minutes. The particle mixture was magnetically washed once in 0.1 M sodium phosphate buffer and resuspended in 0.1 M sodium phosphate buffer at the original particle suspension volume.

One of several surface conjugates were added to the washed particles. Conjugates added include biotin LC hydrazine (Pierce; Fisher Cat# PI-21340) at 2 mg/mL, anti-biotin antibody (clone C6D5.1.1, StemCell Technologies) at 1 mg/mL, streptavidin (Pierce; Fisher Cat# PI-21120) at 0.25 mg/mL and streptavidin hydrazide (Pierce; Fisher Cat# PI-21122) at 0.25 mg/mL. The mixture was then incubated for 2 hours on a tilt-rotator at room temperature. For conditions in which the surface conjugate was streptavidin or streptavidin hydrazide, the sample was split after the initial 2 our incubation and an equal volume of 10% Tween-20 (BioRad Cat# 170-6531) in dH$_2$O was added to one of the volumes and incubated for an additional 30 minutes on a tilt-rotator at room temperature. After incubation, all samples were magnetically washed 3 times with distilled water and resuspended at the initial volume in dH$_2$O.

Conjugated particles were tested in EasySep® mouse CD4 T cell negative selection as described in Example 2. Undesired cells were labeled with biotinylated antibodies directed against cell surface markers. Once labeled, cells were selected by various means as appropriate to the particle surface chemistry and compared to the typical dextran-coated particle strategy. Table 14 summarizes the selection strategy and cell separation results. Of the four surface conjugates tested, streptavidin hydrazide resulted in the most desirable cell separation. Further optimization of the oxidation and conjugation procedure as well as the cell separation conditions would likely improve the performance of the other conjugates. Even under non-optimized conditions, all cell separation strategies tested showed enrichment of the target population. The desired population was measured as CD3$^+$CD4$^+$ using flow cytometric analysis. This example shows that the particle coating can be functionalized.

TABLE 14

Negative Selection of mouse CD4 T cells using alternative selection strategies

| Particle Type | Additional Reagents used in selection of biotinylated-antibody-labeled Cells | % Start Purity | % Enriched Purity | % Recovery |
|---|---|---|---|---|
| EasySep Nanoparticles | TAC directed against biotin on cells and dextran on particles. EasySep Nanoparticles are dextran-coated. | 17 | 91 | 35 |
| EasySep Microparticles | TAC directed against biotin on cells and dextran on particles. EasySep Microparticles are dextran-coated. | 17 | 87 | 39 |
| Particles with unmodified dextran | TAC directed against biotin and dextran. Particles described herein include dextran | 17 | 93 | 39 |
| Particles conjugated to anti-biotin antibody | None | 17 | 54 | 40 |
| Particles conjugated to biotin LC hydrazide | Anti-biotin TAC. Links cells and biotin conjugated particles | 17 | 41 | 39 |
| Particles conjugated to streptavidin | None | 17 | 36 | 49 |
| Particles conjugated to streptavidin with additional Tween-20 incubation | None | 17 | 34 | 41 |
| Particles conjugated to streptavidin hydrazide | None | 17 | 85 | 40 |
| Particles conjugated to streptaviding hydrazide with additional Tween-20 incubation | None | 17 | 84 | 49 |

Conjugated particles were also tested in positive selection of mouse CD4$^+$ T Cells (Cat# 18752 and 18556). Desired cells were labeled with biotinylated anti-CD4 antibody and were then selected by various means as appropriate to the particle surface chemistry. The results are summarized in Table 15. Although the purity and recovery of the target cells is low for the particles, cells selected with these particles did not exhibit significant shifts in the SSC signal during FACS analysis.

TABLE 15

Positive Selection of mouse CD4 T Cells using various selection strategies

| Particle Type | Additional Reagents used in selection of biotinylated-antibody-labeled Cells | % Start | % Purity | % Recovery |
|---|---|---|---|---|
| EasySep Nanoparticles | TAC directed against biotin and dextran. EasySep Nanoparticles are dextran-coated. | 25 | 95 | 32 |
| EasySep Microparticles | TAC directed against biotin and dextran. EasySep Microparticles are dextran-coated. | 25 | 94 | 38 |
| Particles described herein unmodified dextran | TAC directed against biotin and dextran. Particles described herein are dextran-coated. | 25 | 35 | 27 |
| Particles described herein conjugated to anti-biotin antibody | None | 25 | 23 | 17 |

TABLE 15-continued

Positive Selection of mouse CD4 T Cells using various selection strategies

| Particle Type | Additional Reagents used in selection of biotinylated-antibody-labeled Cells | % Start | % Purity | % Recovery |
|---|---|---|---|---|
| Particles described herein conjugated to biotin LC hydrazide | Anti-biotin TAC. Links cells and biotin conjugated particles | 25 | 4 | 2 |
| Particles described herein conjugated to streptavidin hydrazide | None | 25 | 11 | 6 |
| Particles described herein conjugated to streptaviding hydrazide with additional Tween-20 incubation | None | 25 | 9 | 5 |

Example 13

Measurement of Physical Characteristics

Figure 3:
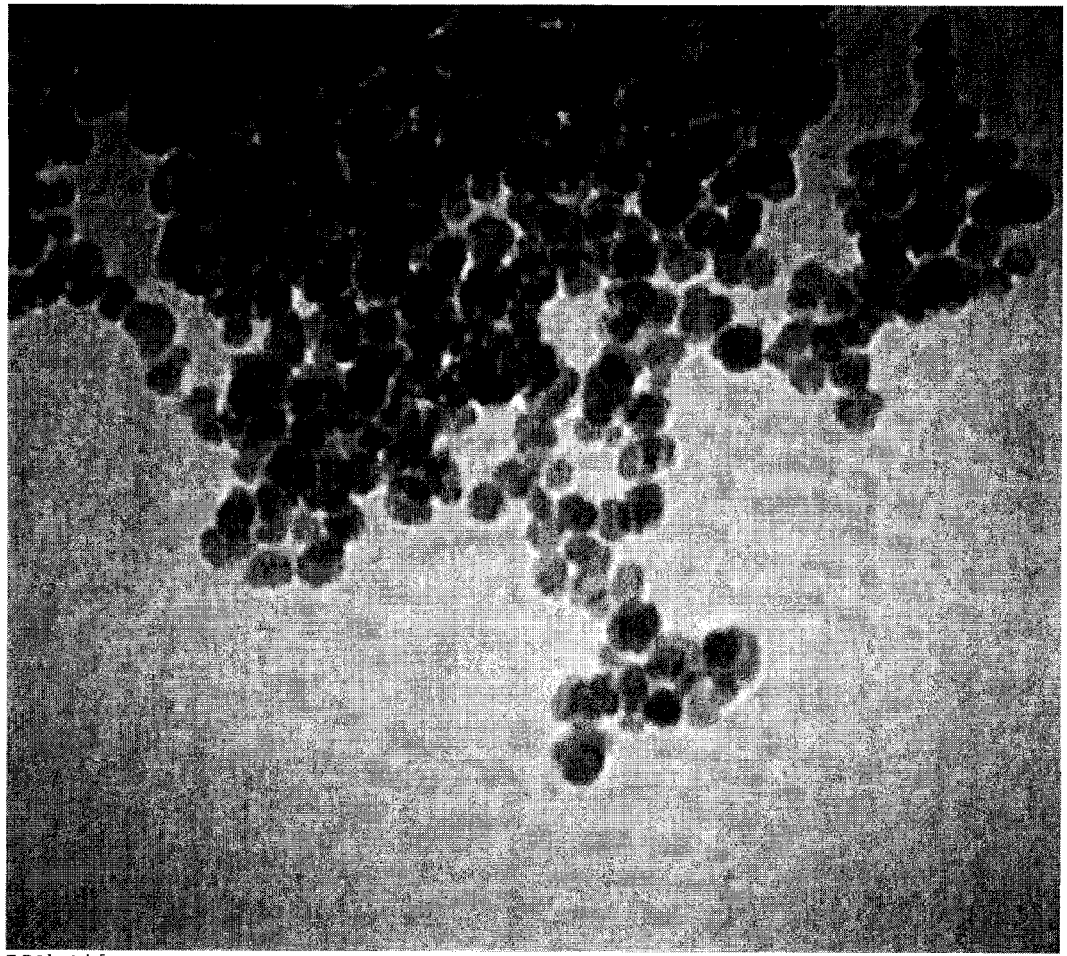
FIG. 3 is a transmission electron micrograph of exemplary particles described herein.

Transmission electron microscopy (TEM) was performed using a Hitachi H-7600 microscope on multiple samples of particles described herein. TEM showed that the ~1 μm diameter particles are composed spherical $Fe_3O_4$ crystals of 5-50 nm diameter clustered together (FIG. 3) where the mean crystal size is 15-20 nm. Different synthesis conditions did not seem to have an appreciable effect on the size of the $Fe_3O_4$ crystals. TEM also shows the presence of the dextran as a passivating layer that surrounds the clusters of $Fe_3O_4$ crystals (FIG. 3b). The dextran appears to hold the $Fe_3O_4$ crystals together into the ~1 μm diameter particles measured using the Horiba instrument and by optical microscopy as described in Example 3.

Thermogravimetric analysis (TGA) was performed using a Seiko SII-6300 equipped with an EX STAR 6000 station for temperature control to determine the mass % of dextran in the particles and a Quantum Design's SP-550 superconducting quantum interference device (SQUID) was used to determine the magnetic moment at 1 T, respectively. The particles have a mass % of dextran between about 17 and 25%. Table 16 shows TGA results for particles synthesized under different conditions and having a range of % dextran from 17 to 20%. Particles with mass % dextran between 17 and 25% performed equally well in CD3 positive selection and the particles showed relatively low side scatter (Example 10).

SQUID measurements on the particles showed that the magnetization varied between 45 and 60 emu/g. The variation in magnetization does not have a significant effect on the time required to magnetically separate labelled cells by either negative or positive selection.

TABLE 16

Mass % of dextran and magnetization of particles synthesized with different conditions

| Sample | Variable | Mass % Dextran | M (emu/g) |
|---|---|---|---|
| A | None, Experiment 1 conditions | 19 | 55.8 |
| B | None, Experiment 1 conditions | 18 | 52.8 |
| C | Experiment 1 conditions where $Fe^{2+}:Fe^{3+}$ = 1:1.8 | n/a | 58.9 |
| D | Experiment 1 conditions where $Fe^{2+}:Fe^{3+}$ = 1:2.1 | 20 | 57.2 |
| E | Experiment 1 conditions where $Fe^{2+}:Fe^{3+}$ = 1:2.2 | 19 | 53.1 |
| F | Experiment 1 conditions where [Fe] = 28 mM | 20 | n/a |
| G | Experiment 1 conditions where [Fe] = 64 mM | 17.5 | 56.7 |
| H | Experiment 1 conditions where [Fe] = 96 mM | 20 | 56.9 |
| I | Experiment 1 conditions where dextran = 5 w/v % | 17 | 57.2 |
| J | Experiment 1 conditions where dextran = 10 w/v % | 18 | 55.8 |

We claim:

1. A magnetic particle comprising:
an aggregate of polysaccharide coated magnetic crystals, each polysaccharide coated magnetic crystal comprising a magnetic crystal and a polysaccharide coating the magnetic crystal,
wherein the magnetic crystals comprise 75 to 83 wt % of the particle.

2. The magnetic particle of claim 1, wherein the magnetic particle has a particle diameter of between 0.5 and 10 microns.

3. The magnetic particle of claim 1, wherein the magnetic particle has a diameter of between 0.9 microns and 2.5 microns.

4. The magnetic particle of claim 1, wherein the magnetic crystals comprise a transition metal oxide.

5. The magnetic particle of claim 4, wherein the transition metal oxide is an iron oxide.

6. The magnetic particle of claim 4, wherein the transition metal oxide comprises at least one of $Fe_2O_3$ and $Fe_3O_4$.

7. The magnetic particle of claim 1, wherein the magnetic crystals have a crystal diameter of between 5 nm and 50 nm.

8. The magnetic particle of claim 1, wherein the polysaccharide is dextran.

9. A magnetic particle comprising an aggregate of polysaccharide coated magnetic crystals, each polysaccharide coated magnetic crystal comprising a magnetic crystal and a polysaccharide coating the magnetic crystal, the magnetic particle prepared according to a method comprising
   a. combining a basic solution with a metal ion solution and allowing the metal ions to oxidize to form the magnetic crystals;
   b. combining the magnetic crystals with a solution of the polysaccharide and allowing the magnetic particles to form, wherein the magnetic crystals comprise 75 to 83 wt % of the particle.

10. A method for separating a first population of cells from a second population of cells suspended in fluid the method comprising:
    a. linking a plurality of magnetic particles according to claim 1 to said first population of cells;
    b. placing said first and second population of cells in a magnetic field; and
    c. recovering one of said first or second populations of cells.

11. The method of claim 10, wherein said magnetic particles are linked to said first population of cells using tetrameric antibody complexes.

12. The method of claim 11, further comprising:
    d. analyzing said first population of cells by FACs, wherein a shift in a side scatter signal of the first population of cells when bound to the magnetic particles is less than 100%.

* * * * *